United States Patent [19]

Carver et al.

[11] Patent Number: 4,589,776
[45] Date of Patent: May 20, 1986

[54] METHOD AND APPARATUS FOR MEASURING OPTICAL PROPERTIES OF MATERIALS

[75] Inventors: David Carver; Thomas A. Tait, both of Fort Collins, Colo.

[73] Assignee: Chiratech, Inc., Fort Collins, Colo.

[21] Appl. No.: 424,919

[22] Filed: Sep. 27, 1982

[51] Int. Cl.$^4$ ............................................. G01N 21/21
[52] U.S. Cl. ..................................... 356/367; 250/225
[58] Field of Search ............................... 356/364–369; 250/225

[56] References Cited

U.S. PATENT DOCUMENTS

| 3,113,171 | 12/1963 | Rouy ................................... 356/367 |
| 3,738,255 | 6/1973 | Chaney et al. . |
| 3,738,756 | 6/1973 | Chaney . |
| 3,740,151 | 6/1973 | Chaney et al. . |
| 3,817,634 | 6/1974 | Barron et al. . |
| 3,901,603 | 8/1975 | White . |
| 4,118,125 | 10/1978 | Gundermann . |
| 4,203,620 | 5/1980 | Bromberg . |
| 4,306,809 | 12/1981 | Azzam . |

OTHER PUBLICATIONS

Swatzky et al., "Apparatus for Direct Recording of Magneto-Optic Rotation and Magnetic Hysteresis", *Rev.-Sci. Instrm.*, vol. 41, pp. 1284–1290, 1970.
Forsythe et al., "An Automatic Recording Magnetooptical Rotation Spectropolarmeter", *Applied Optics*, vol. 6, No. 4, pp. 699–702, 1967.
Tsuda, "Apparatus for Rapid Measurement of Optical Rotation Charges", *Rev. Sci. Instrum.*, vol. 46, No. 10, pp. 1419–1420, 1975.
Hannemann, "A Polarimeter to Measure the Complete State of Polarization of Scattered Solar Radiation", *Contrib Atmos.. Phys.*, vol 48, pp. 76–84, 1975.
Gruenewald et al., "Pressure Jump Method with Detection of Optical Rotation and Circular Dichronism", *Rev. Sci. Instrum.*, vol. 49, No. 6, pp. 797–801, 1978.
Müller, "In vivo Measurement of Glucose Concentration with Lasers", *Horm. Metab. Res.*, Supp. Ser. 33-5, 1979.
Tsuda, "Rapid and Sensitive Optical Rotation Measurement: Kinetics of Conformational Change of Rhodopsin Intermediate", *Photochemistry and Photobiology*, vol. 29, pp. .175–177, 1979.
Saltzman et al., "High Temperature Recording Polarimeter", *Analytic Chemistry*, vol. 27, pp. 1446–1448, 1955.
Keston et al., "Simple Ultrasensitive Spectropolarimeters", *Proc. Fed. Soc. Exptl. Biol.*, vol. 12, pp. 229, 1953.

*Primary Examiner*—Davis L. Willis
*Assistant Examiner*—Matthew W. Koren
*Attorney, Agent, or Firm*—Timothy J. Martin

[57] ABSTRACT

A method and apparatus for measuring optical properties of materials such as optical rotation, depolarization and absorption includes a light source emitting a primary beam of light that is monochromatic, collimated and plane-polarized and a sample cell through which this beam is passed. The primary beam is split into at least two components by a beam splitter and each component is passed through an analyzer, such as a prism. The two analyzers have polarizing axes oriented at a non-zero angle with respect to one another and at preselected angles with respect to the plane of polarization of the original beam. Signals corresponding to the intensities of the components are produced by detectors and then the signals are amplified, digitalized and processed to yield the optical properties. A third test component may alternately be split from the primary beam after it has been passed through the sample with this test component also being detected and processed. A reference component may be split from the primary beam before it is passed through the sample, and the reference component is detected and processed. Existing optical components are assembled to accomplish these steps, and a monochrometer may be used with a selected light source to vary the wavelength of the primary beam.

29 Claims, 2 Drawing Figures

METHOD AND APPARATUS FOR MEASURING OPTICAL PROPERTIES OF MATERIALS

BACKGROUND OF THE INVENTION

The present invention relates to a method and apparatus for measuring various optical properties of materials, including the properties of absorption, optical rotation and depolarization. While the present invention has been constructed to be used as a detector for chromatographic separations, the device may be employed in situations where measurement of these optical properties is desired for a generally transparent, fluid material.

Various polarimeters have been developed in the past, and many of these have been based on a common physical principle that, when plane-polarized light is passed through a material, the plane of polarization of the light is rotated. As is known, nonpolarized light has random orientations, that is, it is composed of light comprised of tranverse waves having all orientations around the axis of propagation, while plane-polarized light is composed of transverse waves having a single orientation with respect to this axis of propagation. Certain substances have the ability to rotate plane-polarized light as it passes through the substance. That is, these substances rotate the orientation of the polarized light about the axis of propagation as the light passes through the substance. The amount of this rotation is related to the substance or material rotating the light, the concentration of the substance, and the path length of light through the substance. Specifically, the specific rotation of the substance is:

$$[\alpha]_\lambda^T = \frac{\alpha}{lc}$$

where:

$[\alpha]_\lambda^T$ = the specific rotation of the substance
$\alpha$ = the observed rotation in degrees
$l$ = the path length in decimeters
$c$ = the mass of the substance in 1 cm$^3$ of solution.

Implied in this equation is that specific rotation is dependent upon the temperature of the substance and the wave length of the light used to measure the rotation. By convention, counterclockwise rotation about the axis of propagation is given a negative sign, and clockwise rotation is given a positive sign. Standard measurements are normally conducted at 25° C. with the sodium d line of 5891 angstroms in order to eliminate the variables of temperature and wavelength.

In most prior art devices, optical rotation is observed by passing the rotated light through an analyzer in the form of a polarizing filter, such as a prism whose optical axis is oriented at an angle with respect to the original plane of polarization. The intensity of the light is diminished by an amount dependent upon the angle of the plane of polarization after rotation and the optic axis of the analyzer. In many prior art devices, the analyzer is oriented in a crossed configuration, i.e. 90°, from the orientation of the plane-polarized lights in order to minimize the amount of light which would pass through the analyzer and reach a detector and therefore the intensity of light at the detector. A sample cell containing the material to be tested is placed between the polarizer and the analyzer so that any rotation of the polarized light as a result of the material will be evidenced by an increase in the intensity of light reaching the detector. Typically, these devices measure the optical rotation by mechanically rotating either the analyzer or the polarizer so that the intensity of light at the detector is reduced to a minimum value or null position. The amount of rotation of the polarizer or analyzer is then exactly equal to the rotation property [$\alpha$] of the sample.

An alternative to mechanical rotation found in the prior art is the rotation twisting of the light by the use of a Faraday rotator. A Faraday rotator is simply a material (optically active or not) that is immersed in a magnetic field along the axis of the transmitted light. The light beam's plane of polarization is rotated proportionally to the strength of the magnetic field component of the Faraday rotator and the length of the light path therethrough.

Examples of these various prior art devices may be found in U.S. Pat. No. 3,510,226 issued May 5, 1970 to Kerry which shows a Faraday coil being used as a compensator for rotation caused by a sample to be measured. U.S. No. Pat. No. 3,361,027 issued Jan. 2, 1968 to Kaye teaches rotation of the polarizer to compensate for the angle of rotation of the sample material while U.S. Pat. No. 4,306,809 issued Dec. 22, 1981 to Azzam teached the use of measuring the rotation of light by means of quarter wave plates.

It is also possible, however, to measure the rotation of the polarized light through the medium by monitoring the intensity of the light at the detector and utilizing this intensity as a basis for calculating the amount of optical rotation. In T. Crumpler et al, "Simple Photoelectric Polarimeter", 27 *Analytical Chemistry* #10 (1955), the polarizer and analyzer filters are oriented at a fixed angle of 45° with respect to one another. This angle provides for the maximum change in intensity at the detector per unit rotation of the light. Inherent limitations of this system were improved upon in various devices wherein a polarized beam was split, either before or after it is passed through a sample cell, and then is subjected to two analyzer polarizing filters oriented at +45° and −45° with respect to the orientation of the first polarizing element. Thus, any optical rotation caused by the sample material would cause an increase in intensity passing through one analyzer while a decrease in intensity in the other analyzer.

Despite these improvements in polarimeters, there still remained a need to provide a method and apparatus for overcoming inherent design limitations of these prior art devices. More particularly, the need remained for an optical measuring device which was able to measure various optical properties of a substance, including the optical rotation, the depolarization, and absorption characteristics of a sample material.

SUMMARY OF THE INVENTION

Accordingly, it is an object of the present invention to provide a novel and useful method and apparatus for measuring various optical parameters of a material.

Another object of the present invention is to provide a method for simultaneously measuring the optical rotation, the depolarization, and the absorption of light passing through a sample of material.

A still further object of the present invention is to provide a method and apparatus for producing signals indicative of optical characteristics of a sample material which signals can be digitalized and enhanced to provide highly accurate information regarding various optical parameters of a sample material.

It is yet another object of the present invention to provide a method and apparatus for measuring various optical parameters of a material in such a manner that the sensitivity of the device can be selectively increased over a diminished range of operation.

To accomplish these objects, the method according to the preferred embodiment of the present invention comprises the steps of producing a beam of plane-polarized light which is then passed through the material whose parameters are sought to be tested. A reference component of this beam may, if desired, be split from the beam before passing the main beam through the material to be tested in order to allow the monitoring of the fluctuation of source light intensity. After passing the main beam of light through the sample material, the beam is split into first and second test components, and then each of these test components is passed through an analyzer in the form of a polarizing element. Each of the analyzers have an optical plane which is oriented at a pre-selected angle with respect to the plane of the initial plane-polarized beam and at a pre-selected angle with respect to one another. By comparing the intensity of the light which passes through each analyzer, measurement of the optical rotation caused by the material is possible since the intensity of the component beams are affected in proportion to the amount of optical rotation. These intensities are detected and are used to generate a pair of analog signals which are then amplified and coverted into digital signals. After the digital signals are generated, the signals are compared to allow mathematical calculation of the optical rotation and removal of measurement errors.

Preferably, the preferred method includes a simultaneous measurement of absorption, depolarization, and rotation of the beam of light passing through the sample material, since the absorption and depolarization properties of the material may affect the intensity of the derivative component beams and thus affect the optical rotation reading. To accomplish the simultaneous measurement of these parameters, the beam is preferably split into three components after it is passed through the sample material, and two of these components are then passed through analyzer elements in the form of polarizers oriented as described above, but which have optical polarizing axes oriented at an angle different than 0° or 90° with respect to one another. The intensity of third component is monitored directly to provide absorption and depolarization data, with the intensity of all three components being measured by a suitable detector means. The intensities of the three components may then be used to calculate the three parameters desired. One or more half wave plates may be placed in the path of the beam after it is passed through the sample cell and before it is split to increase the sensitivity of this method while at the same time decreasing its effective range of measurement.

To implement the above-described method, a polarimeter apparatus is provided which includes a light source that emits a monochromatic beam of collimated, plane-polarized light. This light source can be a laser or a more conventional monochromatic source that emits a beam that is passed through a polarizing filter and collimating elements. A beam splitter may be used to split a reference component from the main beam. A sample cell is provided to hold the material to be measured, and the main beam from the light source is directed through the sample cell. One or more beam splitters intercept the beam of light after it has passed through the sample cell to split this beam into two or three components. At least two of these components are test components and are passed through analyzers in the form of polarizing elements which have their optical axis oriented at a pre-selected angles with respect to the plane of polarization of the original light beam and at a pre-selected angle with respect to one another. Photodetectors then measure the intensity of the various components and produce analog signals which are then individually amplified by a linear amplifier. The amplified signals from the linear amplifier are passed to an analog-to-digital converter which converts all of the analog signals into digital signals. These signals are then compared by appropriate data processor means to generate a display of the characteristics to be measured. Further, optical fiber elements may be provided to conduct the light beam or the beam components during the measurement process.

These and other objects will become more readily appreciated and understood from a consideration of the following detailed description of the preferred embodiment when taken together with the accompanying drawings, in which:

DETAILED DESCRIPTION OF THE PREFERRED EMBODIMENT

The present invention directed to a novel method and optical apparatus for measuring various optical properties of a sample material. Of primary importance to this method and apparatus is its ability to measure the rotation of plane-polarized light passing through the sample material. In addition, since the parameters of absorption and depolarization of the material are desirable parameters to measure, the method and apparatus according to the present invention accomplishes these measurements as well.

As is well known, when plane-polarized light is passed through certain optically active materials, these materials rotate the plane of the polarized light from a few hundredths of a degree to several hundred or even several thousand degrees. The measurement of the specific rotation which a material imparts to a plane-polarized beam of light is a common physical property reported in the literature. The present invention, in addition to measuring this optical rotation, is also directed to measuring the absorption properties of the material to be tested as well as the depolarization effect the material has on a beam of polarized light. Accordingly, the present invention is particularly useful as a polarimeter adapted for chromatographic apparatus.

Figure 1:
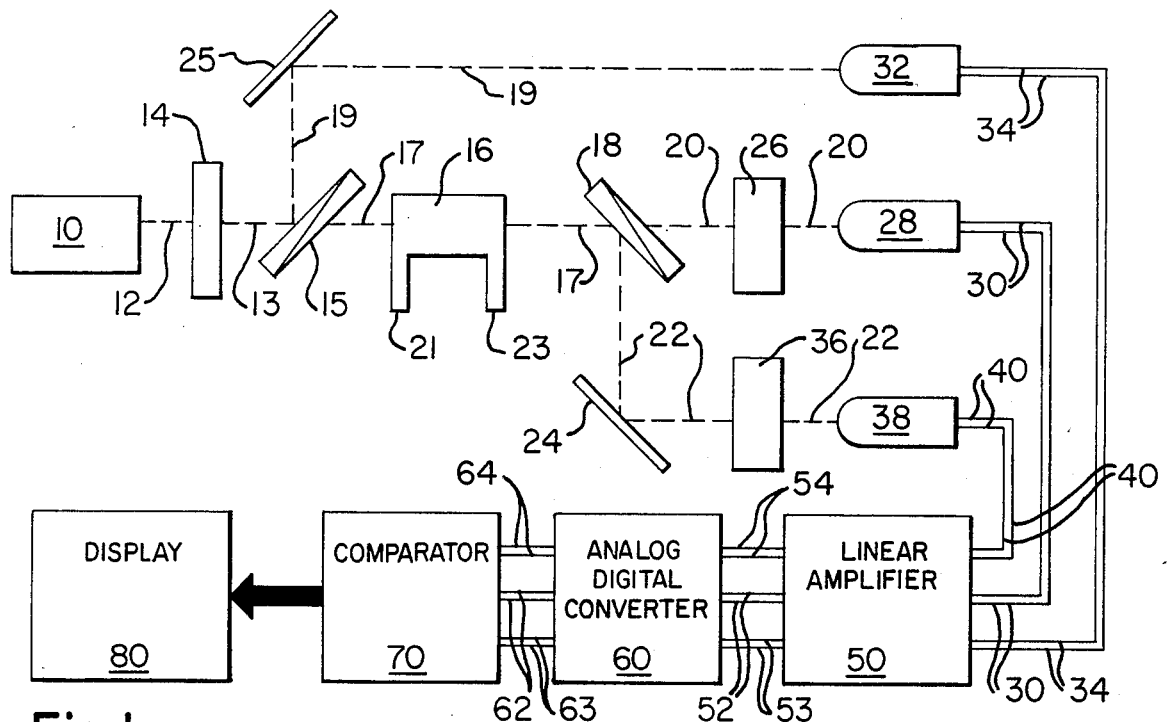
FIG. 1 is a diagramatic representation of the components forming the apparatus for and implementing the method of measuring the optical rotation of a sample material according to the embodiment of the present invention.

Referring now to FIG. 1, there is shown a diagramatic representation of the apparatus according to the preferred embodiment of the present invention which is designed to measure the specific rotation of a beam of plane-polarized light passing through a sample material. In this diagram, a light source 10 is provided which has suitable optics for producing a beam 12 of collimated monochromatic light. Beam 12 is directed through a polarizer element 14 so that it emerges as a collimated beam 13 of monochromatic, plane-polarized light having of polarization that may be referred to as the 0° or reference plane. Beam 13 is then directed through a beam splitter 15 so that it is split into a main beam 17 and a reference component 19. Main beam 17 is then directed a sample cell 16 which contains the material to be studied, and it should be appreciated that sample cell 16 is designed to contain a normally optically active substance. To this end, sample chamber 16 has a relatively transparent cross-section in the direction of beam 17 so that a minimal attenuation of beam 17 occurs as it passes through the cell 16. Thus, any attenuation is a result of interaction between the beam and the material contained in cell 16. Sample cell 16 is a standard flow through cell having an inlet 21 and an outlet 23 so that fluid material may be pumped through cell 16.

Beam 17 is then directed to a beam splitter element 18 which splits beam 13 into a first test component 20 and a second component 22. Component 20 is then passed through a first analyzer element 26 and is then received by a first detector 28. Similarly, component 22 is passed through a second analyzer element 36 and is then received by a second detector 38. Reference component 19 is directed by a mirror 25 to a third detector 32. Suitable optics are provided to direct light beams 12, 13, 17, and components 19, 20 and 22, as exemplified by mirrors 24 and 25. These path elements, such as mirrors 24 and 25, are passive elements whose kind, number and position are determined by the physical dimensions of the device and the relative orientation of the active components, and can be conveniently selected by one ordinarily skilled in the art without the need for experimentation.

Detectors 28, 32 and 38 are preferably photodetector cells which produce an electric signal in response to the intensity of light which each receives. These electric signals are respectively transmitted by way of electrical leads 30, 34 and 40 to a linear amplifier 50 which individually amplifies the electric signals and passes the signals by means of electrical connections 52, 53 and 54 to an analog-to-digital converter 60. The analog information generated by detectors 28, 32 and 38, and amplified by linear amplifier 50, is then converted into digital information by analog-to-digital converter 60. This data then is presented, by means of electrical leads 62, 63 and 64 to comparator processor 70 which processes the digital information to generate a display on display 80 which corresponds to the optical rotation and absorption of beam 17 caused by the sample material in cell 16. It should be understood that this processing may be implemented by processing software according to generally understood principles, and the comparison of the relative intensities of components 20 and 22 allow calculation of the optical rotation caused by the sample material in cell 16. Measurement of reference component 19 permits the user to correct the measurement of absorption and optical rotation by permitting the factoring out of intensity fluctuations occurring at source 10.

From the foregoing, the broad method according to the preferred embodiment of the present invention includes the first step of producing a collimated beam of plane-polarized light and then passing this beam through a sample of material to be measured. This beam is then split into at least first and second test components, such as components 20 and 22, after the beam has passed through the material with each of these first and second components then being passed through an analyzer element in the form of analyzer prisms 26 and 36 shown in FIG. 1 oriented at a pre-selected angle with respect to one another. First and second analog signals are then produced in response to the intensity of light in the first and second components 20 and 22. These first and second analog signals are then each amplified and then converted into first and second digital signals. These first and second digital signals are finally compared to generate an output indicative of the optical rotation of the material. An improvement of this broad method is found in the step of splitting a reference component from the beam prior to passing the beam through the sample cell and then producing a third analog signal in response to the intensity of the reference component, amplifying this third analog signal and converting it into a third digital signal for comparison with the first and second digital signals.

As was shown in FIG. 1, light source 10 and polarizer element 14 provide a beam 13 of plane-polarized, collimated light. A number of different light sources can be employed to generate the collimated, monochromatic plane-polarized beams, but it is preferred that light source 10 be a laser, such as a low pressure helium-neon laser that produces polarized light. If such a laser is used, polarizer element 14 can be eliminated since the beam 12 would already be collimated and plane-polarized as it is emitted from light source 10.

Alternative sources of light may be used as light source 10, for example, an incandescent light may be used if proper filters are provided to filter the incandescent source into a monochromatic beam, and collimating lenses are provided to collimate the light from the incandescent source. In this case, a polarizing element 14, preferably in the form of a Glan-laser prism should be used to polarize the beam as described above. If the requirements of the system are such that a low intensity light beam is acceptable, a light-emitting diode may be used for a light source, and indeed, various laser diodes, which are presently in the development stage, may prove suitable for use in this apparatus and method.

After the beam of plane-polarized light is produced in the first method step, the main beam is passed through the material to be tested with this material being contained in sample cell 16. Sample 16 is a standard flow-through cell that is used in existing polarimeters or for purposes of chromatography and is generally transparent to the wavelength of light comprising beams 13 and 17. After passing beam 17 through the material to be tested, the beam is split into the first and second test components 20 and 22 by a standard beam splitter 18. Although it is preferred that beam splitter 18 produce components 20 and 22 having equal intensities, such a splitting of beam 17 is not an essential requirement since unequal proportion can be compensated for in the data processing operation. It is a requirement of the system, then, that the split ratio of beam splitter 18 be known so that this ratio can be compensated by the software of the comparator processor to generate accurate information. Preferably, beam splitter 18 is a dielectric beam splitter havinq as nearly a ratio of one-to-one as possible.

After beam 17 is split, first and second test component beams 20 and 22 are each passed through polarizing elements or analyzers 26 and 36. It should be appreciated that these analyzers could also take many different forms. In the preferred embodiment, analyzers 26 and 36 are Glan-laser prisms, but other calcite prisms such as Glan-Thompson, Nicol or Wollaston prisms could replace the Glan-laser prisms of the preferred embodiment, but in such case, care must be taken that the prisms are matched to the wavelength of components 20 and 22. Indeed, stacks of plate polarizers or polaroid filters could be used to interact with the polarized light in components 20 and 22. Further, a single Rochon prism having its optical axis oriented at 45° with respect to the reference plane of polarization could replace beam splitter 18 and both analyzers 26 and 36, since it is well known that a Rochon prism both splits the incident beam and interacts as a polarizing element with each component of the polarized light.

After the step of passing the component beams through the analyzers is completed, the preferred method, as set forth above, measures the intensity of the light in each component. It should be appreciated that these intensities may be varied by the analyzers. The reason for this is that the intensity is proportional to the angle between the plane of the plane-polarized light after it has passed through the sample material and the polarizing axis of each analyzer. Since the analyzers have polarizing axes oriented at an angle with respect to one another, the intensity of each component is varied differently by each analyzer, depending upon the angle of the polarizing axis of the incident light. To this end, the polarizing axis of each analyzer 26 and 36 is oriented at a pre-selected angle with respect to the plane of beam 13 and at a pre-selected angle with respect to each other. The interrelationships of these angles are discussed in greater detail below.

Figure 2:
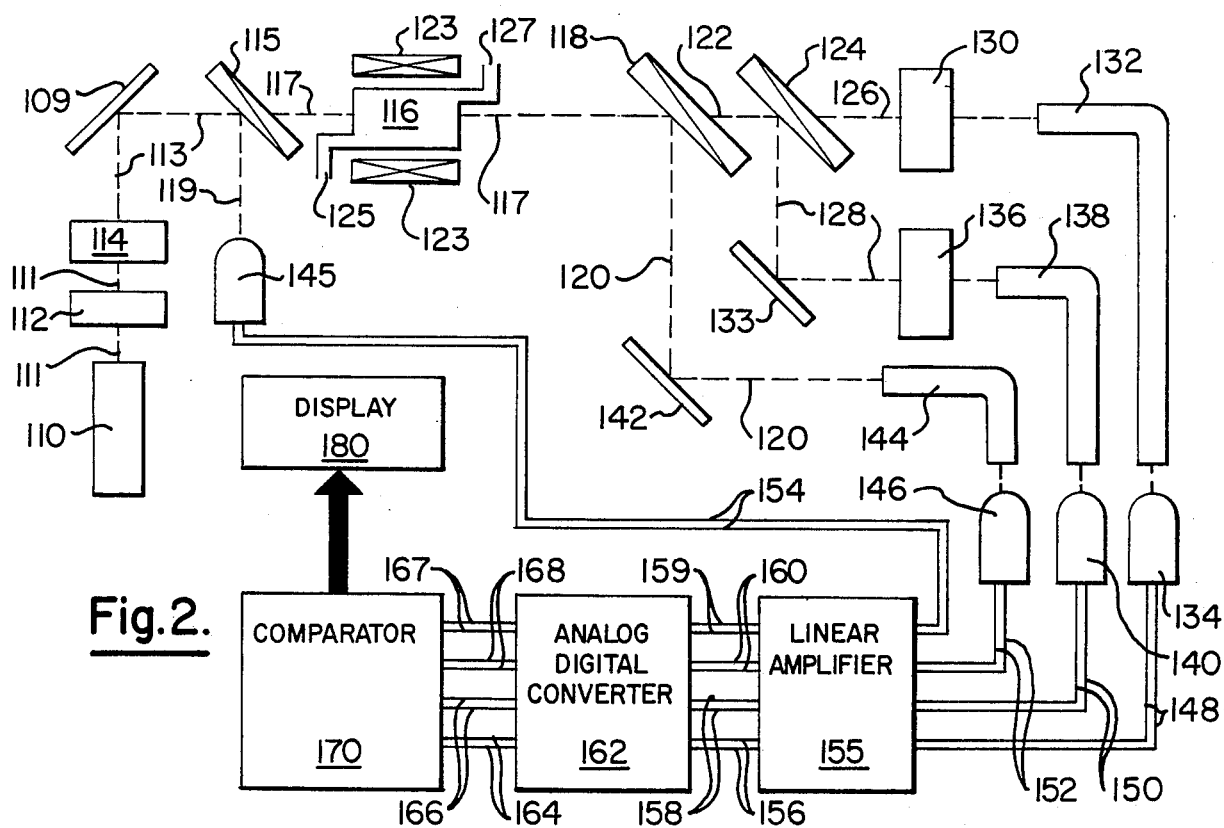
FIG. 2 is a diagramatic representation of the components forming the apparatus for and implementing the method of simultaneously measuring the optical parameters of rotation, depolarization, and absorption according to the present invention.

A second form of the present invention is shown in diagramatic representation in FIG. 2 and is a more sophisticated system for simultaneously measuring the optical rotation, depolarization and absorption of light resulting from interaction with the sample material. Here, a light source 110 is provided which produces a collimated beam 111 of light. Beam 111 is directed through a monochrometer 112, which may optionally be used in this system but is not required, and then through a polarizing element 114 to produce a plane-polarized beam 113 of collimated light having a wavelength governed by monochrometer 112. Should monochrometer 112 be eliminated, it is necessary that optical elements be employed to ensure that beam 113 is monochromatic. In the alternative, a laser source could be used, as discussed above.

Beam 113 is then directed by mirror 109 to a beam splitter 115 which splits beam 113 into a main beam 117 and a reference beam 119. Main beam 117 is directed through a sample cell 116. Sample cell 116 includes a Faraday coil 123 which extends around sample cell 116 as is known in the art so that the energizing of coil 123 to selected levels causes a normally non-optically active material in cell 116 to become optically active. Sample cell 116 has an inlet 125 and an outlet 127 which permits fluid sample material to be pumped through cell 116.

After beam 117 has passed through cell 116, it is directed toward a beam splitter 118. Upon reaching first beam splitter 118, beam 117 is divided into a first test component 120 and second component 122 with the intensity of these components being dependent upon the characteristics of first beam splitter 118. Preferably beam splitter 118 has a ratio of approximately nine to one so that component 122 is nine times more intense than first test component 120. Second component 122 is then directed to a second beam splitter 124 which divides component 122 into two test components having generally equal intensities. These test components are designated as second test component 126 and third test component 128. Second test component 126 is then directed to a first analyzer 130 as discussed above, and is then passed through a first fiber optic element or bundle 132 so that it is directed to a first detector 134. Third test component 128 may be directed by mirror 133 through a second analyzer 136 after which component 128 is passed through fiber optic element or bundle 138 and directed to a second detector 140. Finally, first test component 120 is directed by mirror 142 so that it is passed through a third fiber optic element or bundle 144 and directed to a third detector 146. It should be noted that there is preferably no analyzer prism in the path of first component 120 before it reaches detector 146. Similarly, reference component 119 is directed to a fourth detector 145.

Detectors 134, 140, 145, and 146 are preferably photodetectors, such as phototransistors, photoresistors or photomultipliers, each of which responds to the intensity of incident light thereon either to produce an electric signal corresponding to that intensity or modulate a signal proportionally to the intensity of its respective incident light. The signal produced by detector 134 is transmitted by way of wires 148 to a linear amplifier 155. Similarly, detector 140 produced a signal which is transmitted by way of wires 150 to amplifier 155, and detector 146 transmits a signal by way of wires 152 to linear amplifier 155, and detector 145 transmits a signal by way of wires 154 to amplifier 155. Each of the signals from detectors 134, 140, 145, and 146 are analog signals which are individually amplified by linear amplifier 155 with the four amplified signals then being transmitted respectively, by wires 156, 158, 159, and 160 to an analog-to-digital converter 162 where each analog signal is converted into a corresponding digital signal. These digital signals are then transmitted by way of leads 164, 166, 167, and 168 respectively, to a comparator 170 which processes the signals and then transmits the composite information to a display 180.

This second embodiment provides a second broad method for measuring optical parameters. According to the second embodiment of the invention, this method broadly includes several of the steps discussed with the apparatus according to FIG. 1, with this method being directed to measuring the parameters of absorption, depolarization and rotation of a beam of light in an optically active material. This method broadly includes the steps of producing a collimated beam of plane-polarized light and then passing this beam through a sample of the material to be tested. This beam of light is split into first, second and third components after it is passed through the sample of material such as components 120, 126 and 128 shown in FIG. 2. Two of these components, such as components 126 and 128 are then passed through a polarizing element such as analyzers 130 and 136 having polarizing axes oriented at an angle with respect to one another. First, second and third analog signals are generated in response to the intensity of these components, with the second and third analog signals being generated in response to the intensity of the light in each of the second and third components after they have passed through the respective polarizing elements. These analog signals are then compared to determine the above-designated parameters. As further refinements of this method, the first, second and third analog signals are amplified and may be converted into digital signals prior to the step of comparing the signals to determine the desired parameters.

From the above-described system, it is possible to measure three discrete parameters of a sample material placed in sample cell 116. These three parameters include the absorption properties of the material at wavelength of light generated by light source 10, the depolarization of a beam of plane-polarized light passing through the material or caused by the optical components of the system, and the optical rotation of a beam of plane-polarized light passing through the material or caused by the optical components of the system. It is particularly important to monitor and determine all three of these parameters since the absorption and depolarization, if not known, may cause error in the calculation of the optical rotation of the beam. Further, it should be noted that, although the fluctuation of intensity of the source will affect the amount of signal at the detector, this fluctuation and the absorption of light by the sample material are indistinguishable. Accordingly, they may be considered to be the same parameter. Accordingly, it is highly desirable to eliminate these parameters in order to accurately calculate the amount of rotation which the polarized light undergoes as it passes through the sample material.

To determine these parameters, it should be appreciated that the voltage output of the three-detector system may be expresses as:

$$V_1 = K_1 r_1 I (1-d) \cos^2(u_1+a) + d/2$$

$$V_2 = K_2 r_2 I (1-d) \cos^2(u_2+a) + d/2$$

$$V_3 = K_3 r_3 I$$

where, $V_1$ = Magnitude of signal from first detector in response to the intensity of light thereon
$V_2$ = Magnitude of signal from second detector in response to the intensity of light thereon
$V_3$ = Magnitude of signal from third detector in response to the intensity of light thereon
$K_1$ = Response factor of first detector
$K_2$ = Response factor of second detector
$K_3$ = Response factor of third detector
$r_1$, $r_2$ and $r_3$ = constants determined from the optical system as is known in the art which includes the beam splitting ratios of the beam splitters
$I$ = Initial intensity of light
$d$ = The decimal fraction that the light is depolarized
$u_1$ = The angle of the optical axis of first analyzer (i.e. Analyzer 130) with respect to the plane of polarization the beam (i.e. beam 112) prior to passing through the sample cell
$u_2$ = The angle of the optical axis of the second analyzer (i.e. Analyzer 136) with respect to the plane of polarization of the beam (i.e. beam 112) prior to passing through the sample cell
$a$ = Angle of optical rotation of the beam (112) due to the sample material in the sample cell The constants $K_1$, $K_2$, $K_3$, $r_1$, and $r_2$ are factors determined by the optics of the system and the various components of the system, and may be analytically measured and incorporated within the software of comparator 170. Thus, for purposes of discussion, it is possible to consider these constants to be equal to one since they do not add any effect to the result as long as they are compensated for by comparator 170. Also, setting $D = d \, I$, the above equation can be simplified as follows:

$$V_1 = (I-D)\cos^2(u_1+a) + D/2$$

$$V_2 = (I-D)\cos^2(u_2+a) + D/2$$

$$V_3 = I$$

The above system of equations expresses a relationship between the three parameters for a sample material and optical system. Accordingly, a mathematical function may be expressed as dependent upon the variables for which it is sought to be solved. This function, $f(i,a,d)$, may be solved for an arbitrary point $(I, a, D)$. The proof that such solution can be had may be found in writing by the following Jacobian matrix of the function:

$$J_f = \begin{pmatrix} \cos^2(u_1+a) - 2(I-D)\cos(u_1+a)\sin(u_1+a) & \tfrac{1}{2} - \cos^2(u_1+a) \\ \cos^2(u_2+a) - 2(I-S)\cos(u_2+a)\sin(u_2+a) & \tfrac{1}{2} - \cos^2(u_2+a) \\ 1 & 0 & 0 \end{pmatrix}$$

The determinant of the Jacobian matrix may be taken to give the equation:

$$det(J_f) = (-2)(I-D)[\cos(u_1+a)\sin(u_1+a)(\tfrac{1}{2} - \cos^2(u_2+a)) - \cos(u_2+a)\sin(u_2+a)(\tfrac{1}{2} - \cos^2(u_1+a))]$$

Thus, from this determinant it is seen that a unique solution of the three parameters I, D, and a is possible.

It should be understood from the above equation, that the determinant of the Jacobian matrix is never zero except when $D = I$ or when $|u_1 - u_2| = (90°)(n)$ where n is an integer greater than or equal to zero. It is a requirement of the system that the determinant be nonzero in order that a unique solution in the variables I, D, and a be obtained. Accordingly, in order to provide a unique solution in these variables, the angular orientation between the optical axes of analyzers 130 and 136 must not be perpendicular to one another. At the same time, the maximum sensitivity of the instrument for optical rotation occurs when one of the analyzer prisms has an angle of $+45°$ with respect to the reference plane of the plane-polarized beam and the other analyzer prism has an optical axis oriented at an angle of $-45°$ with respect to the reference plane of the plane-polarized beam. The reason for this is that rotation of the beam of light will cause an increase in light at one photodetector corresponding to one of the analyzers while the same rotation will cause a decrease in the intensity of light at the other detector. Hence, the signal difference for the two detectors is doubled which increases the sensitivity of the device. Thus, for example, maximum sensitivity of the device to optical rotation for the embodiment of the invention shown in FIG. 1 would occur when analyzer prisms 26 and 36 are oriented at $+42°$ and $-45°$ with respect to the plane of polarization of the initial beam of light 17 before it has passed through cell 16. A general expression for this is where one prism is oriented at an angle of $(+45°)(n)$ and the other prism is oriented at an angle of $(-45°)(p)$ with respect to the reference plane and perpendicularly to one another where n and p are odd positive integers. However, with respect to the embodiment shown in FIG. 2, such orientation of the analyzer prisms 130 and 136, while increasing the sensitivity of the device to the measurement of optical rotation, eliminates the ability of the device to measure depolarization.

Similarly, it should be appreciated from the above equations that the maximum sensitivity of the devices shown in FIGS. 1 and 2 for measuring the depolarization of the light as a result of the sample material and the optics of the system occurs when the analyzer prisms 26, 36 or analyzer prisms 130, 136 will occur when the polarizing axes of these prisms are oriented at 180° with respect to each other and with one of the analyzer prisms oriented perpendicularly to the reference plane. This occurs where one prism is oriented at an angle of (+90°)(n) and the other prism is oriented at an angle of (−90°)(n) with respect to the reference plane where n is an odd positive integer. This orientation of the analyzer prisms, though, minimizes the response of the polarimeter apparatus to rotations of the plane-polarized light as it passes through the sample material.

Based on the above, it has been found that a compromise of these extrema enhances the operation of the polarimeter shown in FIG. 2 where the user seeks to monitor all three parameters discussed. Specifically, in the configuration shown in FIG. 2, a suitable range for operation has been found wherein one of the analyzer prisms 130, 136 is oriented within angular range of approximately +5°−+40° with respect to a secondary reference plane which secondary reference plane is oriented at an angle of (+45°)(n) with respect to the primary reference plane where n is an integer. The other of analyzer prisms 130, 136 is then oriented at an angle within −5° to −40° with respect to a tertiary reference plane which tertiary reference plane is oriented at an angle of (+45°)(p) with respect to the primary reference plane where p is an integer. This relative orientation preferably requires that the ranges of the angles for the two prisms not be coextensive, that is, that they not identically overlap although this is not an absolute requirement of the system. Indeed, it is found highly suitable to have one analyzer prism oriented at +30° with the other analyzer prism being oriented at −30° with respect to the reference plane. This orientation provides a suitable sensitivity to depolarization while at the same time maintains a high level of sensitivity for optical rotation. It should be noted that the absorption characteristics are monitored by the intensity of the light as detected by detector 146 with this occuring without the use of an analyzer prism, so that the orientation of analyzer prisms 130 and 136 do not affect the sensitivity of the device to attenuation of the intensity of light caused by absorption or fluctuation of light source 110. Accordingly, component 120 provides a reference beam permitting removal of error from the calculations of optical rotation caused by variations in the intensity of light not caused by optical rotation or depolarization of the light.

Further, the use of optional monochrometer 112 allows the user to vary the wavelength of light beam 111 after it has passed through monochrometer 112. Thus, the user can "tune" the system to a selected wavelength or "scan" over a range of wavelengths during a selected time interval. By utilizing beam splitter 115 to produce a reference component 119 and the detection of reference component 119 by detector 145, errors otherwise introduced by the fluctuation of the intensity of light from source 110 or fluctuations due to the interaction of monochrometer 112 with the source beam can be factored out of the calculation of the desired parameters in comparator processor 170 software.

Further advantages of the present system may be provided by the use of analog-to-digital converters 60, 162. With respect to the analog-to-digital converter, prior art devices usually monitor analog signals, and, maximize or minimize these signals through mechanical rotation of components. Measurement of the amount of mechanical rotation is then used to calculate the optical rotation of the plane-polarized beam resulting from its passage through the sample material. The present invention, though, converts these analog signals to digital signals which permits the mathematical removal of errors that would be otherwise overlooked in the analog signal, with this removal of errors being accomplished in the software package programmed in the respective comparator processor 70, 170. This software package forms no part of the present invention, and it should be appreciated that this program does not affect the functioning or sensitivity of the components described with respect to the embodiments shown in FIG. 1 and FIG. 2. Thus, different programs may be used to mathematically enhance the data processing of the digital signals generated by the apparatus and methods according to the above described embodiments of the present invention.

While the foregoing invention has been described with respect to the preferred embodiments of the present invention, it is to be understood that the scope of this invention is defined by the following claims limited only by the prior art. Accordingly, various changes and modifications of this invention are included within the scope of these claims and may be made without departing from the scope of the invention described herein.

We claim:

1. Apparatus for measuring optical properties of a generally transparent sample material, comprising:

a light source means for producing a substantially monochromatic beam of collimated plane-polarized light along a first reference plane of polarization at a selected wavelength;

a sample cell for containing the material to be measured, said sample cell positioned in said beam and having transparent portions to allow passage of said beam there through;

a first beam splitter positioned in said beam on a side of said cell opposite the light source and operative to split said beam into first and second test components;

first analyzer means positioned in the optical path of said first test component and having a first polarizing axis oriented at an angle within a first range of +5° to +40° with respect to a secondary reference plane which secondary reference plane is oriented at an angle of (+45°) (n) with respect to said first reference plane wherein n is an integer, said first analyzer means for changing the intensity of said first component as a function of the angle between said first polarizing axis and said first reference plane of polarization;

second analyzer means positioned in the optical path of said second test component and having a second polarizing axis oriented at a non-zero angle with respect to said first polarizing axis and at an angle within a second range of −5° to −40° with respect to a tertiary reference plane which tertiary reference plane is oriented at angle of ( +45°) (p) with respect to said first reference plane where p is an integer, said second analyzer means for changing the intensity of said second component as a function of the angle between said second polarizing axis and said first reference plane of polarization;

first and second detector means receiving said first and second test components after they have passed through said first and second analyzer means, respectively, for producing first and second signals corresponding to the intensities of said first and second test components, respectively; and processing means for comparing said first and second signals and for producing an output corresponding to said optical properties.

2. Apparatus according to claim 1 wherein said first and second signals are analog signals, said processing means including a linear amplifier operatively to amplify said signals independently of one another and analog to digital converter means for converting said analog signals into corresponding digital signals.

3. Apparatus according to claim 2 wherein said first and second detector means includes first and second photomultipliers.

4. Apparatus according to claim 1 wherein said light source means includes a laser.

5. Appartus according to claim 1 wherein said light source means includes a monochromatic light source, a first optical element to collimate light from said light source and a second optical element to polarize said beam along said first reference plane of polarization.

6. Apparatus according to claim 1 including a monochrometer means associated with said light source and said sample cell for selectively varying the wavelength of said monochromatic beam.

7. Apparatus according to claim 2 wherein said first and second detector means includes first and second photocells oriented in the path of said first and second test components, respectively.

8. Apparatus according to claim 1 wherein said first and second analyzer means are first and second polarizing prisms, respectively.

9. Apparatus according to claim 8 wherein said first and second prisms are Glan-laser prisms matched to the wavelength of light in said beam.

10. Apparatus according to claim 1 wherein said first beam splitter and said first and second analyzer means are a Rochon prism.

11. Apparatus according to claim 1 including a second beam splitter positioned in the optical path of said beam ahead of said first beam splittter and operative to divide said beam into a secondary beam and a third test component, said first beam splitter receiving said secondary beam and operative to divide said secondary beam into said first and second test components, and including third detector means receiving said third test component for producing a third signal corresponding to the intensity of said third test component, said processing means for comparing said first, second, and third signals.

12. Apparatus according to claim 11 wherein the ratio of the intensity of said secondary beam to the intensity of said third test component is approximately 9:1.

13. Apparatus according to claim 11 including first, second and third fiber optic means for transmitting said first, second and third test components, respectively, to said first, second and third detector means, respectively.

14. Apparatus according to claim 1 or 11 further including a third beam splitter positioned in the path of said beam ahead of said sample cell and operative to split a reference component beam from said beam, and a fourth detector means receiving said reference component beam for producing a fourth signal corresponding to the intensity of said reference component beam, said processing means for comparing all said signals.

15. Apparatus according to claim 1 wherein said sample cell is a Faraday cell.

16. Apparatus for measuring optical parameters of a generally transparent sample material, comprising:

a sample cell adapted to hold the sample material to be tested;

a light source means for producing a substantially monochromatic beam of collimated, plane-polarized light oriented at a primary reference plane of polarization and for directing said beam through said sample cell;

beam splittting means on a side of said sample cell opposite said light source means for splitting said beam into first, second and third light test components;

first, second and third detector means for receiving, respectively, said first, second and third test components and producing first, second and third signals, respectively, in response to the intensity of the light of its associated component;

a first analyzer element positioned in be path of one of said first, second and third test components between said beam splitting means and an associated detector means and a second analyzer element position in the path of another one of said first, second and third components between said beam splitting means and an associated detector means, said first analyzer element having a first optical axis oriented at a positive angle less than 45° with respect to a secondary reference plane and said second analyzer having a second optical axis oriented at a negative angle greater than −45° with respect to a tertiary reference plane where said secondary reference plane is oriented at an angle of (45°) (n) with respect to said primary reference plane and said tertiary reference plane is oriented at an angle of (45°) (p) with respect to said primary reference plane where n and p are integers and where the said tertiary plane is at an angle with respect to said secondary plane that is different from 45; and processing means for comparing said first, second and third signals and generating an output corresponding to said parameters.

17. Apparatus according to claim 16 wherein said first optical axis is oriented at an angle within a range of +5° to +40° with respect to said secondary reference plane and said second optical axis is oriented at an angle within a range of −5° to '40° with respect to said tertiary reference plane.

18. Apparatus according to claim 16 wherein said first optical axis is oriented at an angle of approximately +30° with respect to said secondary plane and said second optical axis is oriented at an angle of approximately −30° with respect to said tertiary plane.

19. Apparatus according to claim 16 including first, second and third fiber optic elements in the paths of said first, second and third components, said fiber optic elements adapted to conduct each said component to its respective detector means.

20. Apparatus according to claim 16 wherein said processing means includes a linear amplifier operative to amplify said first, second and third signals, an analog-to-digital converters to convert each of said amplified signals into digital signals and a comparator means for comparing said digital signals and outputting said parameters.

21. Apparatus according to claim 16 including a second beam splitting means ahead of said sample cell for splitting a reference component from said beam and a fourth detector for receiving said reference component and producing a fourth signal, said processing means comparing all said signals.

22. Apparatus according to claim 21 including a monochrometer means associated with said light source for selectively varying the wavelength of said beam.

23. A method for measuring the optical rotation properties of a relatively transparent, optically active material comprising the steps of:
producing a primary beam of plane-polarized light oriented at a first reference plane of polarization;
passing said primary beam through said material;
splitting said primary beam into a least first and second test components after said beam has passed through said material;
passing said first test component through a first analyzing element having a first polarizing axis oriented at an angle within a first range of $+5°$ to $+40°$ with respect to a secondary reference plane which secondary reference plane is oriented at an angle of $(\pm 45°)$ (n) with respect to said first reference plane where n is an integer;
passing said second test component through a second test component through a second analyzing element having a second component through a second analyzing element having a second polarizing axis oriented at a non-zero angle with respect to said first polarizing axis and at an agnel within a second range of $-5°$ to $-40°$ with respect to a tertiary reference plane which tertiary reference plane is oriented at an angle of $(\pm 45°)$ (p) with respect to said first reference plane where p is an integer;
producing first and second analog signals corresponding to the intensity of said first and second test components after each has passed through its respective analyzing element;
amplifying said first and second analog signals;
converting said first and second analog signals into first and second digital signals after they have been amplified; and
comparing said first and second digital signals to generate an output indicative of the optical rotation of said material.

24. The method according to claim 23 including the steps of splitting a reference component said primary beam prior to passing said primary beam through said sample and producing a third analog signal corresponding to the intensity of said reference component, converting said signal into a third digital signal and comparing said third digital signal with said first and second digital signals.

25. The method according to claim 24 including the step of varying the wavelength of said primary beam.

26. The method of measuring the parameters of absorption, depolarization and rotation of a beam of light in an optically active material comprising the steps of:
producing a collimated primary beam of plane-polarized light;
passing said primary beam through a sample of said material;
splitting said primary beam into first, second and third test components after said beam has passed through said material;
passing each of said second and third test components through a polarizing element;
producing a first signal corresponding to the intensity of said first test component and second and third signals corresponding to said second and third test components after each of said second and third test components has passed through its respective polarizing element; and
comparing said first, second and third signals to determine said parameters.

27. Claim 26 further including the step of subjecting said sample material and said beam while in said sample material to a controlled electromagnetic field.

28. The method according to claim 26 including the steps of splitting a reference component from said primary beam prior to passing said primary beam through said sample and producing a fourth signal corresponding to the intensity of said reference component and comparing all said signals.

29. The method according to claim 28 including the step of varying the wavelength of said primary beam.

* * * * *

UNITED STATES PATENT AND TRADEMARK OFFICE
CERTIFICATE OF CORRECTION

PATENT NO.   : 4,589,776
DATED        : May 20, 1986
INVENTOR(S)  : David Carver and Thomas A. Tait It is certified that error appears in the above-identified patent and that said Letters Patent is hereby corrected as shown below:

Column 4, line 4, delete "optical" and substitute --polarizing--; line 4, after "at", delete "a"; line 29, before "embodiment", insert --preferred--.
Column 10, line 63, delete "(+42°)", substitute -- +45° --
Column 12, line 57, delete "(+45°)", substitute -- (±45°) --; line 58, delete "wherein", substitute --where n --. Column 13, line 1, delete "(+45°)", substitute -- (±45°) --. Column 14, line 57, delete " '40°", substitute -- -40° --. Column 15, line delete "component through a second analyzing element having a second"; line 39, delete "agnel", substitute --angle--.

Signed and Sealed this

Twenty-fifth Day of April, 1989

*Attest:*

DONALD J. QUIGG

*Attesting Officer*   Commissioner of Patents and Trademarks